(12) United States Patent
Cadwallader et al.

(10) Patent No.: US 8,299,120 B2
(45) Date of Patent: Oct. 30, 2012

(54) THERAPY FOR MULTIPLE SCLEROSIS

(75) Inventors: Dianne Cadwallader, Auckland (NZ); Timothy Meakin, Auckland (NZ)

(73) Assignee: Lypanosis Pte Limited, Singapore (SG)

( * ) Notice: Subject to any disclaimer, the term of this patent is extended or adjusted under 35 U.S.C. 154(b) by 0 days.

(21) Appl. No.: 11/628,266

(22) PCT Filed: Jun. 2, 2005

(86) PCT No.: PCT/NZ2005/000110
§ 371 (c)(1),
(2), (4) Date: Dec. 4, 2006

(87) PCT Pub. No.: WO2005/118070
PCT Pub. Date: Dec. 15, 2005

(65) Prior Publication Data
US 2007/0225368 A1 Sep. 27, 2007

(30) Foreign Application Priority Data
Jun. 3, 2004 (NZ) ........................................ 533370

(51) Int. Cl.
*A01N 37/00* (2006.01)
(52) U.S. Cl. .................. 514/546; 514/558; 514/903
(58) Field of Classification Search .................. 514/558, 514/903
See application file for complete search history.

(56) References Cited

U.S. PATENT DOCUMENTS

| | | | |
|---|---|---|---|
| 6,696,491 B2 | 2/2004 | Meakin et al. | |
| 7,411,079 B2 | 8/2008 | Cadwallader et al. | |
| 2003/0153620 A1 | 8/2003 | Meakin et al. | |
| 2003/0171432 A1 | 9/2003 | Meakin et al. | |
| 2005/0004216 A1 | 1/2005 | Cadwallader et al. | |
| 2005/0137257 A1 | 6/2005 | Meakin et al. | |

FOREIGN PATENT DOCUMENTS

| | | | |
|---|---|---|---|
| WO | WO-99/52508 A1 | | 10/1999 |
| WO | WO 00/64436 | * | 2/2000 |
| WO | WO 01/85162 | * | 11/2001 |
| WO | WO-01/85163 A1 | | 11/2001 |
| WO | WO-01/85164 A1 | | 11/2001 |
| WO | WO03/018731 | | 3/2003 |
| WO | WO-03/026640 A1 | | 4/2003 |
| WO | WO-03/045374 A1 | | 6/2003 |

OTHER PUBLICATIONS

Copaxone: Multiple sclerosis symptoms: Bowel problems Problems in bowel movements—either constipation or diarrhea—can accompany MS (Capaxone.com/aboutMS/bowel.aspx).*
Bernd et al. ("Treatment and treatment trials in multiple sclerosis." Curr Opin Neurol (2007);20:286-93).*
Bitsch et al. (Ann Neurol 2001;49:793-796).*
Annapurna et al (Indian Journal of Pharmacology 2002; 34: 3-15).*
Gennaro, Alfonso. Remington's: Pharmaceutical Science. 17th Edition. Easton, PA: Mack Publishing Company, 1985).*
R. Porto (Sexologies (2011); 20:15-19).*
Copaxone:Multiple sclerosis symptoms: Bowel problems Problems in bowel movements—either constipation or diarrhea—can accompany MS (Capaxone.com/aboutMS/bowel.aspx). (2009).*
Brusaferri et al. (2000) *J Neurol* 247:435-442.
Fisk et al. (1994) *Clin Infect Dis* 18(S1):S79-83.
Goodin (2002) *Neurol* 58:169-178.
Goodin (2002). *Disease Modifying Therapies in Multiple Sclerosis*, report of the Therapeutics and Technology Assesment Subcommittee of the American Academy of Neurology, 63 pages.
Griffiths (1994) *J Clin Pharm Ther* 19:219-222.
Kraft et al. (1986) *Arch Phys Med Rehabil* 67:164-168.
Krupp (2001) *Curr Neurol Neurosci Rep* 1:294-298.
Krupp et al. (1988) *Arch Neurol* 45:435-7.
Munschauer (1997) *Clin Ther* 19(5):883-893.
Ritvo et al. (1996) *J Clin Epidemiol* 49:467-472.
Ritvo et al. (1997). *Multiple Sclerosis Quality of Life Inventory: A User's Manual*. National Multiple Sclerosis Society, New York, 65 pages.
Schwid (2002) *J Rehab Res Dev* 39(2):211-224.
van Winsen (2005) *J Clin Endocrinol Metab* 90:734-740.
Wiendl (2003) *Ex Opin Investig Drugs* 12(4):689-712.

* cited by examiner

*Primary Examiner* — Frederick Krass
*Assistant Examiner* — Chris Simmons
(74) *Attorney, Agent, or Firm* — Morrison & Foerster LLP (57) ABSTRACT

The invention relates to a method of ameliorating multiple sclerosis and/or the symptoms of multiple sclerosis in a mammal, which comprises administering or having self administered to the mammal an effective amount of (a) cetyl myristate or (b) cetyl myristate and cetyl palmitate. In preferred embodiments the mode of administration is oral and both cetyl myristate and cetyl palmitate are administered.

10 Claims, 7 Drawing Sheets

THERAPY FOR MULTIPLE SCLEROSIS

This is a nationalization of PCT/NZ2005/000110 filed 2 Jun. 2005 and published in English.

FIELD OF THE INVENTION

The present invention relates to a therapy for multiple sclerosis. More particularly, the present invention is directed to the amelioration of multiple sclerosis and/or the symptoms of multiple sclerosis.

BACKGROUND

Multiple sclerosis (MS) is an inflammatory disease of the Central Nervous System (CNS) and is predominantly a disease of the "white matter" tissue. White matter is made up of nerve fibers which are responsible for transmitting communication signals both internally within the CNS and between the CNS and the nerves supplying the rest of the body.

In people affected by MS, patches of damage called plaques or lesions appear in seemingly random areas of the CNS white matter and at the site of a lesion, a nerve insulating material, called myelin, is lost.

Clinically, MS is a hard condition to characterize because it is very unpredictable and variable and depending on which areas of the CNS is affected and how badly it is damaged, the type and severity of symptoms can vary greatly.

No two people get MS in exactly the same way and the expression of each individual's disease is unique, however, the different courses of the disease, both within an individual and within the whole population, principally differ in their timing, location and severity. In general, people suffering from MS can experience partial or complete loss of any function that is controlled by, or passes through, the brain or spinal cord.

Symptoms of multiple sclerosis include weakness of one or more extremities, paralysis, tremor of one or more extremities, muscle spasticity (uncontrollable spasm of muscle groups), muscle atrophy, movement dysfunction that is slowly progressive beginning in the legs with associated numbness, decreased or abnormal sensation in any area of the body, tingling, facial pain, extremity pain, loss of vision, double vision, eye discomfort, decreased coordination, loss of balance, decreased ability to control small or intricate movements, walking/gait abnormalities, vertigo, cognitive difficulties including decreased memory, spontaneity, loss of judgment, ability to think abstractly, depression, slurred speech, difficulty speaking or understanding speech, extreme fatigue associated with becoming tired easily. Additional symptoms that may be associated with this disease include constipation, hearing loss and positive Babinski's reflex. Such symptoms can affect the quality of life of a MS sufferer.

There is no known cure for multiple sclerosis at this time. Treatment is aimed at controlling symptoms and maintaining the physical, cognitive and mental functions of a sufferer to insure their quality of life is maximized.

Current treatments for patients suffering from MS with relapsing-remitting symptoms include an immune modulating therapy that requires injection under the skin or in the muscle once or several times a week. This may be in the form of interferon (such as AVONEX™ or BETASERON™) or another medicine called glatiramer acetate (COPAXONE™).

Steroids can also be given to a patient to decrease the severity of attacks when they occur. This causes the immune system to shut down to stop cells from causing inflammation. Other medicines such as BACLOFEN™, TIZANDINE™ or DIAZEPAM™ may be used to reduce muscle spasticity. Cholinergic medications may be helpful to reduce urinary problems, antidepressant medications can also help with mood or behavior symptoms and AMANTADINE™ may be given for fatigue.

It is an object of the present invention to provide a method of treatment and/or prophylaxis of the symptoms of multiple sclerosis in a sufferer or at least to provide the public with a useful choice.

BRIEF DESCRIPTION OF THE INVENTION

In a first aspect the present invention provides the use of (a) cetyl myristate or (b) a combination of cetyl myristate and cetyl palmitate in the preparation of a medicament for ameliorating multiple sclerosis and/or the symptoms of multiple sclerosis, in a mammal in need thereof, such as a human.

In certain preferred embodiments, the medicament contains at least 50% w/w cetyl myristate, such as 50 to 98% w/w of cetyl myristate.

In certain preferred embodiments, the ratio of cetyl myristate to cetyl palmitate w/w in the medicament is in the range of between 80:20 to 99:1 w/w, such as about 95:5 w/w.

In one embodiment the medicament comprises a dosage unit comprising from 5 to 400 mg of cetyl myristate or a combination of cetyl myristate and cetyl palmitate.

In certain embodiments the medicament is in the form of a dosage unit such as a capsule or is in the form of a liquid.

In certain preferred embodiments, the medicament further includes one or more pharmaceutically acceptable excipients and/or diluents, such as one or more of the following: silicon dioxide, calcium phosphate, magnesium oxide and/or a trace element.

In certain preferred embodiments the symptom of multiple sclerosis is fatigue.

In another aspect the present invention provides a method of ameliorating multiple sclerosis and/or the symptoms of multiple sclerosis in a mammal in need thereof, which comprises or includes administering or having self administered to such mammal an effective amount of (a) cetyl myristate or (b) cetyl myristate and cetyl palmitate.

In certain preferred embodiments the administration is orally, preferably either of a mixture of cetyl myristate and cetyl palmitate, or serially.

In certain preferred embodiments the administration is with a mixture of cetyl myristate and cetyl palmitate wherein the cetyl myristate comprises at least 50% w/w, such as 50 to 98% w/w, of the mixture.

In certain preferred embodiments the medicament is in the form of a dosage unit such as a capsule or is in the form of a liquid.

In certain preferred embodiments, the administration is by means of one or more capsules.

In certain preferred embodiments, cetyl myristate and cetyl palmitate and/or an admixture are administered in the ratio of about 80:20 to 99:1 (w/w), such as 95:5 (w/w) respectively.

In certain preferred embodiments the symptom of multiple sclerosis is fatigue.

In a further aspect the present invention provides the use of cetyl myristate in the preparation of a medicament for co-administration with cetyl palmitate to ameliorate multiple sclerosis and/or the symptoms of multiple sclerosis in a mammal in need thereof.

In another aspect the present invention provides the use of cetyl palmitate in the preparation of a medicament for co-administration with cetyl myristate to ameliorate multiple sclerosis and/or the symptoms of multiple sclerosis in a mammal in need thereof.

In yet a further aspect, the present invention provides the use of cetyl palmitate and cetyl myristate in the manufacture of a combined preparation for simultaneous, separate or sequential administration for amelioration of multiple sclerosis and/or the symptoms of multiple sclerosis in a mammal in need thereof.

Although the invention is broadly as defined above, it is not limited thereto and also includes embodiments of which the following description provides examples.

DESCRIPTION OF THE FIGURES

The invention will now be described in more detail and with reference to the accompanying figures in which.

DETAILED DESCRIPTION OF THE INVENTION

As defined above, the present invention relates to a method for treating multiple sclerosis, and in particular for reducing or ameliorating the symptoms of multiple sclerosis such as fatigue.

The applicants have surprisingly found that the administration of cetyl myristate (particularly by ingestion) and particularly of cetyl myristate in conjunction with cetyl palmitate, provides an effective treatment of multiple sclerosis, and in particular the symptoms of multiple sclerosis such as fatigue, weakness, tiredness, depression and double vision.

Cetyl myristate and cetyl palmitate are both known compounds and are available from commercial sources.

In certain preferred embodiments which will be described in more detail below, the method of the present invention involves the administration to a patient suffering from multiple sclerosis of both cetyl myristate and cetyl palmitate, either serially or in admixture. In certain preferred embodiments the cetyl myristate and cetyl palmitate are administered orally, and preferably in admixture.

In certain preferred embodiments a mixture of cetyl myristate and cetyl palmitate suitable for use in the invention is synthesised from starting materials utilising the procedures as disclosed in the applicant's earlier PCT International Patent Publication No. WO 03/018731. The full contents of WO 03/018731 are incorporated herein by reference. This synthetic method involves reacting both myristic acid and palmitic acid with cetyl alcohol at an elevated temperature in the presence of at least one acid catalyst and at least one aromatic hydrocarbon. The aromatic hydrocarbon fraction then contains the mixture of cetyl myristate and cetyl palmitate from whence it can be crystallised.

In particular embodiments, the synthetic method described in WO 03/018731 involves reacting cetyl alcohol with a mixture of myristic acid and palmitic acid in an aromatic liquid hydrocarbon such as toluene or xylene, in the presence of phosphoric acid catalyst, at an elevated temperature (preferably between 65° C. and 140° C.), for a period of time (preferably about 8 to about 45 hours).

Following crystallisation of the mixture of cetyl myristate and cetyl palmitate, the crystallised form can then be ground up, dissolved and mixed with a suitable general pharmacy liquid to be administered to a person. The crystals may conveniently be dissolved in hot water before adding to a pharmacy liquid, which may conveniently be sugar syrup available from most pharmaceutical companies. The liquid may be made up to a concentration of about 70% w/v.

Alternatively the crystals may be ground up into a powder and combined with one or more pharmaceutically acceptable excipients or diluents, such as magnesium oxide, silicon oxide and fine di-calcium phosphate. This powder can then be transferred into capsules for oral ingestion into the body. The capsules used may conveniently be VEGICAP™ that are non-gelatin containing.

In other embodiments, a medicament suitable for use in the present invention containing either cetyl myristate alone or in combination with cetyl palmitate can be obtained using cetyl myristate and cetyl palmitate separately available from commercial sources and handled as described above.

In certain preferred embodiments, a mixture of cetyl myristate and cetyl palmitate for use in a medicament to be administered to a patient in accordance with the present invention may contain at least 50% w/w cetyl myristate, such as about 50% to about 98% w/w cetyl myristate (such as about 60% to about 98% w/w, such as about 70% to about 98% w/w, such as about 80% to about 98% w/w, such as about 90% to about 98% w/w, such as about 92% to about 97% w/w, such as about 93% to about 96% w/w).

In certain preferred embodiments, the ratio of cetyl myristate to cetyl palmitate to be administered to the patient, either serially or in admixture, may be from about 80:20 to 99:1 w/w, such as from about 85:15 to about 97:3 w/w, such as about 95:5 w/w cetyl myristate:cetyl palmitate.

The mode of administration is preferably oral. The dosage unit may conveniently be either a capsule to be swallowed where the active ingredient(s) is in the form of a wax-like solid or alternatively is an orally consumable liquid composition (e.g. made up with a general pharmacy type carrier such as methyl cellulose).

Other modes of administration can include transdermal and suppository delivery.

The administration process may involve either orally ingesting the formulation, such as swallowing capsules or drinking a liquid formulation containing cetyl myristate or a mixture of cetyl myristate and cetyl palmitate either on an empty stomach or not. The number of capsules or liquid taken depends on the size and severity of the person's condition.

In certain embodiments, a dosage unit comprising cetyl myristate or a mixture of cetyl myristate and cetyl palmitate for use in the present invention may contain between about 5 and 400 mg (such as from 20 to 380 mg, such as from 30 to 370 mg, such as from 40 to 360 mg, such as from 50 to 350 mg, such as from 100 to 350 mg, such as from 200 to 350 mg, such as from 300 to 350 mg) of either cetyl myristate alone, or of a mixture of cetyl myristate and cetyl palmitate, conveniently in the proportions described above.

An example of a dosage regime of the present invention suitable for an adult suffering from multiple sclerosis involves taking at least 4 capsules, 3 times daily of a preferred dosage unit as herein described for a period of at least six to eight weeks, although improvement in the patient may occur before this time period. The dosage can then be reduced to suit the individual. This dosage may be increased or decreased depending on the symptoms of the patient.

For a child the number of capsules taken is generally about half or less of the dosage required for an adult patient.

Similarly, by way of example, for a liquid formulation, where an amount of liquid equivalent to at least 4 capsules containing 350 mg of cetyl myristate or a mixture of cetyl myristate and cetyl palmitate is prescribed that is to be taken 3 times daily, then at least 4200 mg of cetyl myristate or the mixture of cetyl myristate and cetyl palmitate will need to be consumed.

It has been observed that in particular that in patients who suffer fatigue associated with MS this fatigue has decreased when such patients have been administered a composition as described herein at the prescribed rate.

As indicated above, the present invention encompasses the use of compositions comprising cetyl myristate as the sole active agent. However, it has been found that enhanced benefits occur where there is a small proportion of cetyl palmitate (as described above) in addition to the cetyl myristate.

Fatigue, a common and frequently disabling symptom in MS, has been shown to interfere with activities of daily living and to rank with the most troubling symptoms reported by MS patients (Kraft, G. H., Freal, J. E., Coryell, J. K. (1986). Disability, disease duration and rehabilitation services needs in multiple sclerosis: patient perspectives. *Archives of Physical Medicine and Rehabilitation,* 67, 164-168). Several studies have confirmed the prevalence and importance of fatigue as an MS symptom, particularly in relation to mental health (Ritvo, P. G., et. al., (1996) Psychosocial and neurological predictors of mental health in multiple sclerosis. *Journal of Clinical Epidemiology,* 49, 467-472; and Krupp, L. B., et. al., (1988) Fatigue in multiple sclerosis. *Archives of Neurology*).

In the Multiple sclerosis Quality of Life Inventory (MSQLI), fatigue is assessed with a modified form of the Fatigue Impact Scale (FIS) (Fisk, J. D., et al., (1994). Measuring the Functional Impact of Fatigue: Initial Validation of the Fatigue Impact Scale. *Clinical Infectious Disease,* 18 (Suppl 1) S79-83), based on items derived from interviews with MS patients about how fatigue impacts their lives. This instrument, i.e., FIS, provides an assessment of fatigue effects in terms of physical, cognitive and psychosocial functioning.

This same instrument was used to measure fatigue in patients who carried out the trial described in the Trial Examples below, both before and after taking a composition as described herein at the prescribed rate.

Prior to selection for the MSQLI, the full scale FIS was evaluated with MS patients, Chronic Fatigue Syndrome patients and individuals diagnosed with essential hypertension (Ritvo et. al., (1997) Multiple sclerosis Quality of Life Inventory: A User's Manual. National Multiple sclerosis Society).

A copy of the questionnaire from the National Multiple sclerosis Society is shown in Table 1 below where patients are asked a series of questions and to rate how they are feeling with a number from between 0 to 4. For further details relating to the questionnaire, see Ritvo et. al., (1997) Multiple sclerosis Quality of Life Inventory: A User's Manual. National Multiple sclerosis Society.

TABLE 1

Patient's Name: __________  Date: __/__/__  
                                                             month day year  
ID#: __________  Test#: 1 2 3 4

MODIFIED FATIGUE IMPACT SCALE (MFIS)

Following is a list of statements that describe how fatigue may affect a person. Fatigue is a feeling of physical tiredness and lack of energy that many people experience from time to time. In medical conditions like MS, feelings of fatigue can occur more often and have a greater impact than usual. Please read each statement carefully, and then circle the one number that best indicates how often fatigue has affected you in this way during the past 4 weeks. (If you need help in marking your responses, tell the interviewer the number of the best response.) Please answer every question. If you are not sure which answer to select, please choose the one answer that comes closest to describing you. The interviewer can explain any words or phrases that you do not understand.

Because of my fatigue during the past 4 weeks....

| | | Never | Rarely | Sometimes | Often | Almost always |
|---|---|---|---|---|---|---|
| 1. | I have been less alert. | 0 | 1 | 2 | 3 | 4 |
| 2. | I have had difficulty paying attention for long periods of time. | 0 | 1 | 2 | 3 | 4 |
| 3. | I have been unable to think clearly. | 0 | 1 | 2 | 3 | 4 |
| 4. | I have been clumsy and uncoordinated. | 0 | 1 | 2 | 3 | 4 |
| 5. | I have been forgetful. | 0 | 1 | 2 | 3 | 4 |
| 6. | I have had to pace myself in my physical activities. | 0 | 1 | 2 | 3 | 4 |
| 7. | I have been less motivated to do anything that requires physical effort. | 0 | 1 | 2 | 3 | 4 |
| 8. | I have been less motivated to participate in social activities. | 0 | 1 | 2 | 3 | 4 |
| 9. | I have been limited in my ability to do things away from home. | 0 | 1 | 2 | 3 | 4 |
| 10. | I have had trouble maintaining physical effort for long periods. | 0 | 1 | 2 | 3 | 4 |

TABLE 1-continued

| | | | | | | |
|---|---|---|---|---|---|---|
| 11. | I have had difficulty making decisions. | 0 | 1 | 2 | 3 | 4 |
| 12. | I have been less motivated to do anything that requires thinking. | 0 | 1 | 2 | 3 | 4 |
| 13. | my muscles have felt weak. | 0 | 1 | 2 | 3 | 4 |
| 14. | I have been physically. uncomfortable. | 0 | 1 | 2 | 3 | 4 |
| 15. | I have had trouble finishing tasks that require thinking. | 0 | 1 | 2 | 3 | 4 |
| 16. | I have had difficulty organizing my thoughts when doing things at home or at work. | 0 | 1 | 2 | 3 | 4 |
| 17. | I have been less able to complete tasks that require physical effort. | 0 | 1 | 2 | 3 | 4 |
| 18. | my thinking has been slowed down. | 0 | 1 | 2 | 3 | 4 |
| 19. | I have had trouble concentrating. | 0 | 1 | 2 | 3 | 4 |
| 20. | I have limited my physical activities. | 0 | 1 | 2 | 3 | 4 |
| 21. | I have needed to rest more often or for longer periods. | 0 | 1 | 2 | 3 | 4 |

From this table the items of the MFIS can be aggregated into three subscales being: —Physical, Cognitive, and Psychosocial, as well as into a total MFIS score. All items are scaled so that higher scores indicate a greater impact of fatigue on a patient's activities.

Physical Subscale:

This scale can range from 0-36. It is computed by adding the raw scores on the following questions as depicted in Table 1 4+6+7+10+13+14+17+20+21

Cognitive Subscale:

This scale can range from 0-40. It is computed by adding the raw scores on the following questions as depicted in Table 1 1+2+3+5+11+12+15+16+18+19

Psychosocial Subscale:

This scale can range from 0-8. It is computed by adding the raw scores on the following questions as depicted in Table 1 8+9

Total MFIS Score:

The total MFIS score can range from 0-84. This score can be computed by adding together the scores on the Physical+Cognitive+Psychosocial subscales.

The present invention will now be described in more detail with reference to the following non-limiting examples.

Trial Examples

The results of trials in accordance with the present invention are set out below. Each briefly describes the patient's condition before and after the stated treatment using dosage forms of the invention, each dosage form containing about 350 mg of a mixture of cetyl myristate and cetyl palmitate as manufactured by a process as described in WO 03/018731, comprising 95% cetyl myristate and 5% cetyl palmitate (w/w). In addition added excipients were present in the non-gelatin two part capsule case.

Patient JT is Female

JT had been diagnosed with MS for approximately 4 years. Her prescribed medication included a subcutaneous injection of P interferon (AVONEX™), evening primrose and half an aspirin. Fatigue, depression, general weakness and being constantly tired were her main symptoms from MS and she suffered from these symptoms despite being on the prescribed medication.

Figure 2:
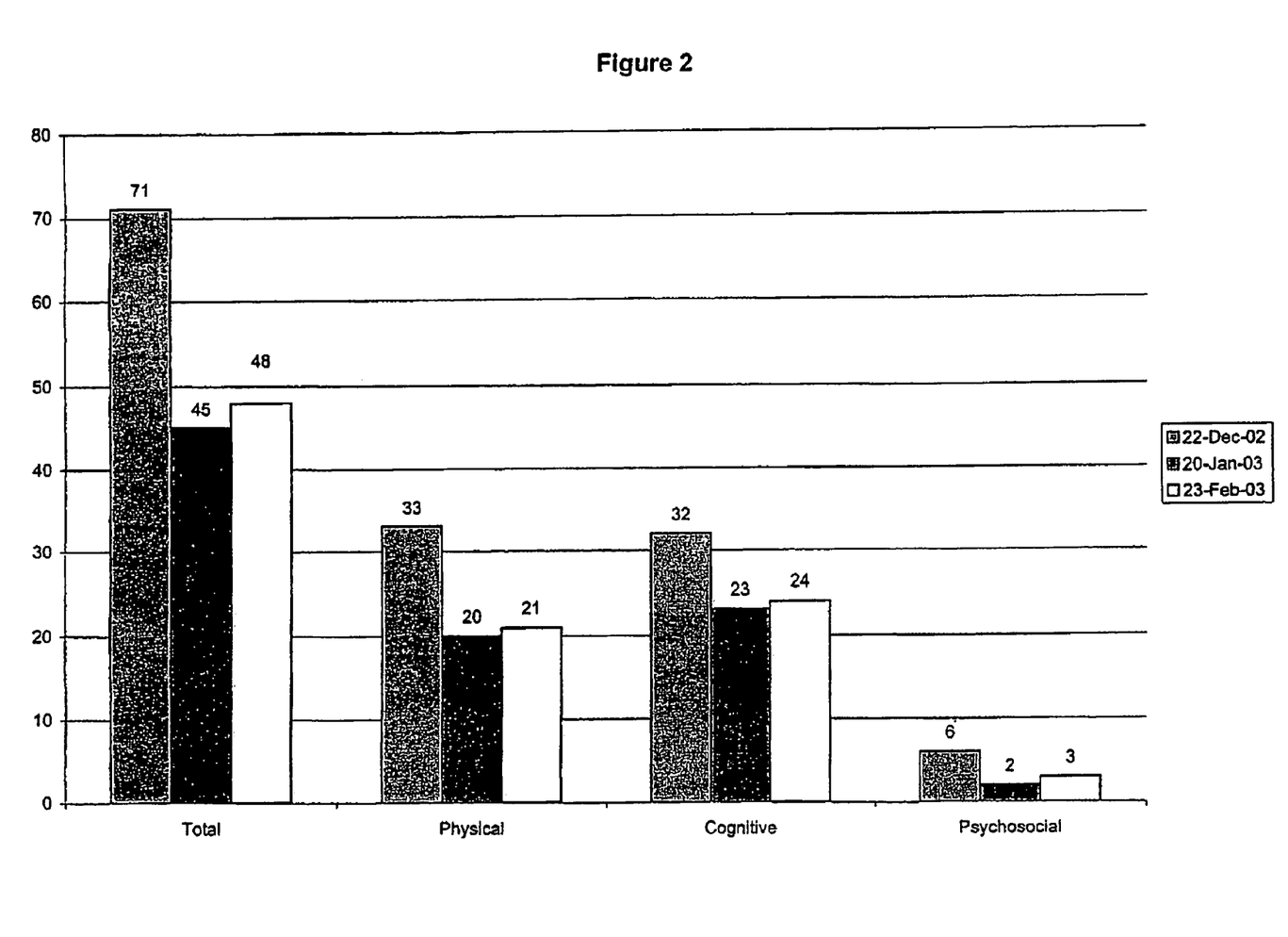
FIG. 2 shows the breakdown of the total score into physical, cognitive and psychosocial for patient MS.
Figure 3:
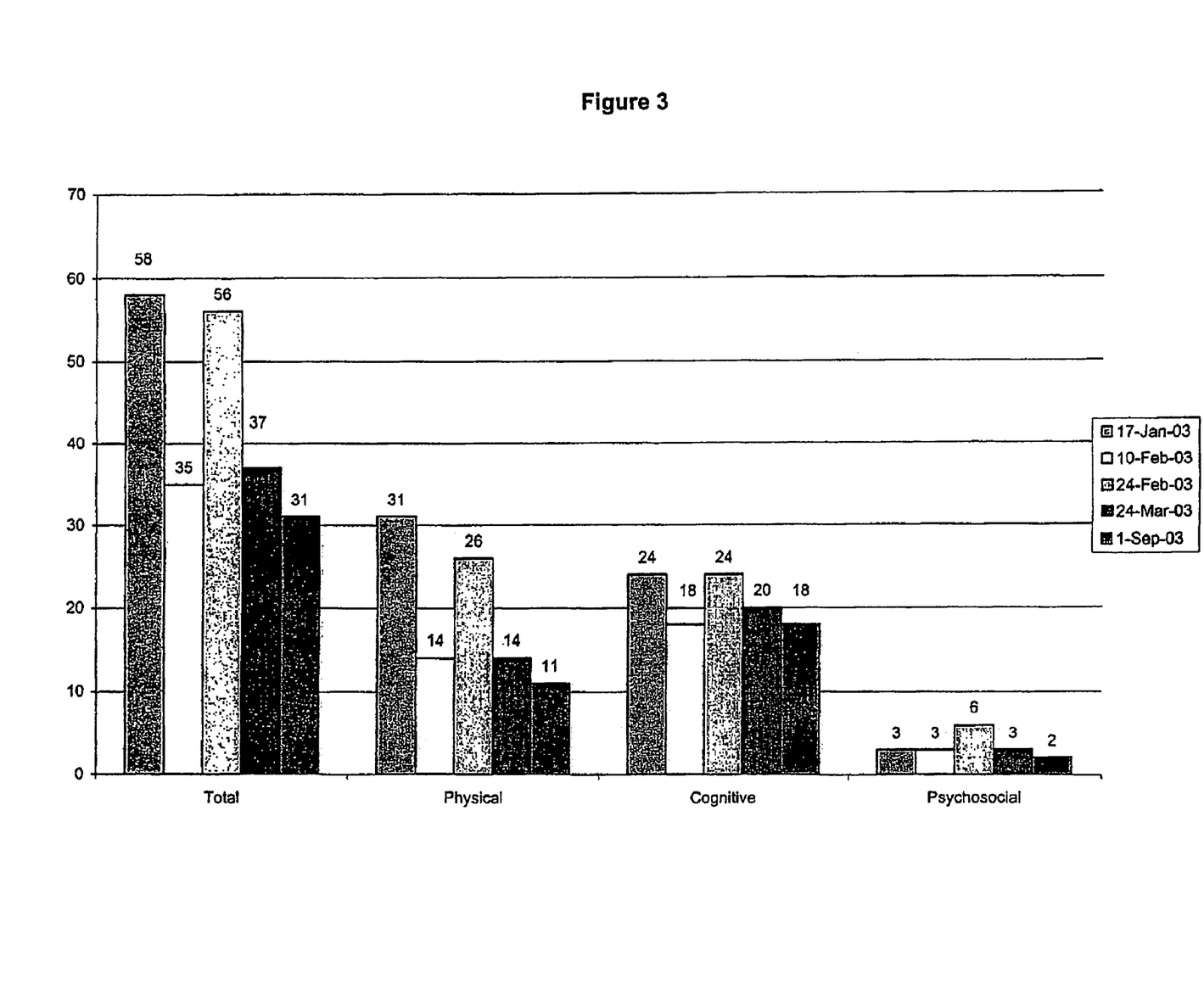
FIG. 3 is similar to FIG. 2 but for patient JT.

At her first appointment on 17 Jan. 2003, JT carried out the MFIS questionnaire as set out in Table 1 to determine her total MFIS score which started at 58 (see FIG. 2). JT was then provided with capsules containing cetyl myristate and cetyl palmitate in accordance with the invention described herein which were taken in groupings of 4 capsules 3 times a day.

Figure 7:
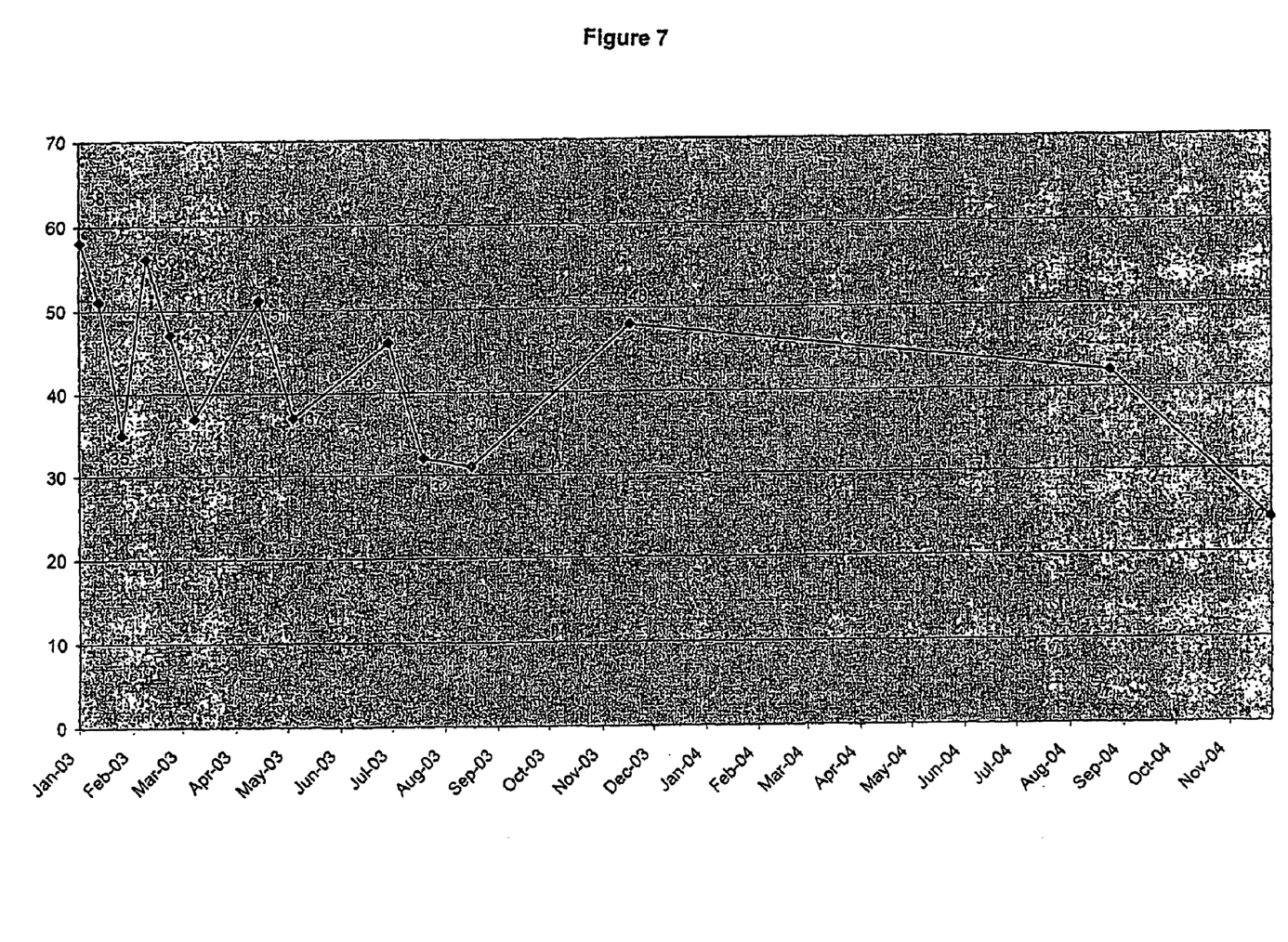
FIG. 7 is similar to FIG. 1 but for patient JT.

After three weeks she carried out a further MFIS questionnaire to determine her total MFIS score which had decreased to 35 (see FIG. 2). She then stopped taking the capsules and after 2 weeks her total MFIS score had almost returned to the initial levels (see FIG. 2). Since then she has regularly taken the capsules and has seen a steady decrease in her total MFIS. FIG. 7 shows the results of further MFIS questionnaires carried out by JT up to November 2004. She no longer takes the prescribed medication and her depression has improved such that she recently married something she had not contemplated before taking the invention due to her MS symptoms.

Patient KB is Female

D.O.B: Dec. 5, 1961 AGE: 45 years old

Initially diagnosed with Multiple Sclerosis in May 2003 after an episode of tramping and noticing a left leg weakness. Her symptoms also included general fatigue and double vision. Her leg weakness was initially treated as a nerve root.

The subsequent MRI scan revealed extensive matter disease involving both hemispheres, the left cerebral hemisphere and the spinal cord consistent with multiple sclerosis.

She had been reviewed by Dr EM at the Auckland City Hospital regarding this condition.

KB then had a consultation with Dr TM and discussed her multiple sclerosis condition and her options. She was offered capsules containing cetyl myristate and cetyl palmitate as described herein to use at 4 capsules×3 daily. Subsequently she began taking the capsules after completing the Modified Fatigue Impact Scale, hereafter referred to as "MFIS" (Fisk et al. Measuring the functional impact of fatigue: initial validation of the fatigue impact scale. *Clin Infect Dis*. 1994b January; 18 Suppl 1:S79-83).

Figure 1:
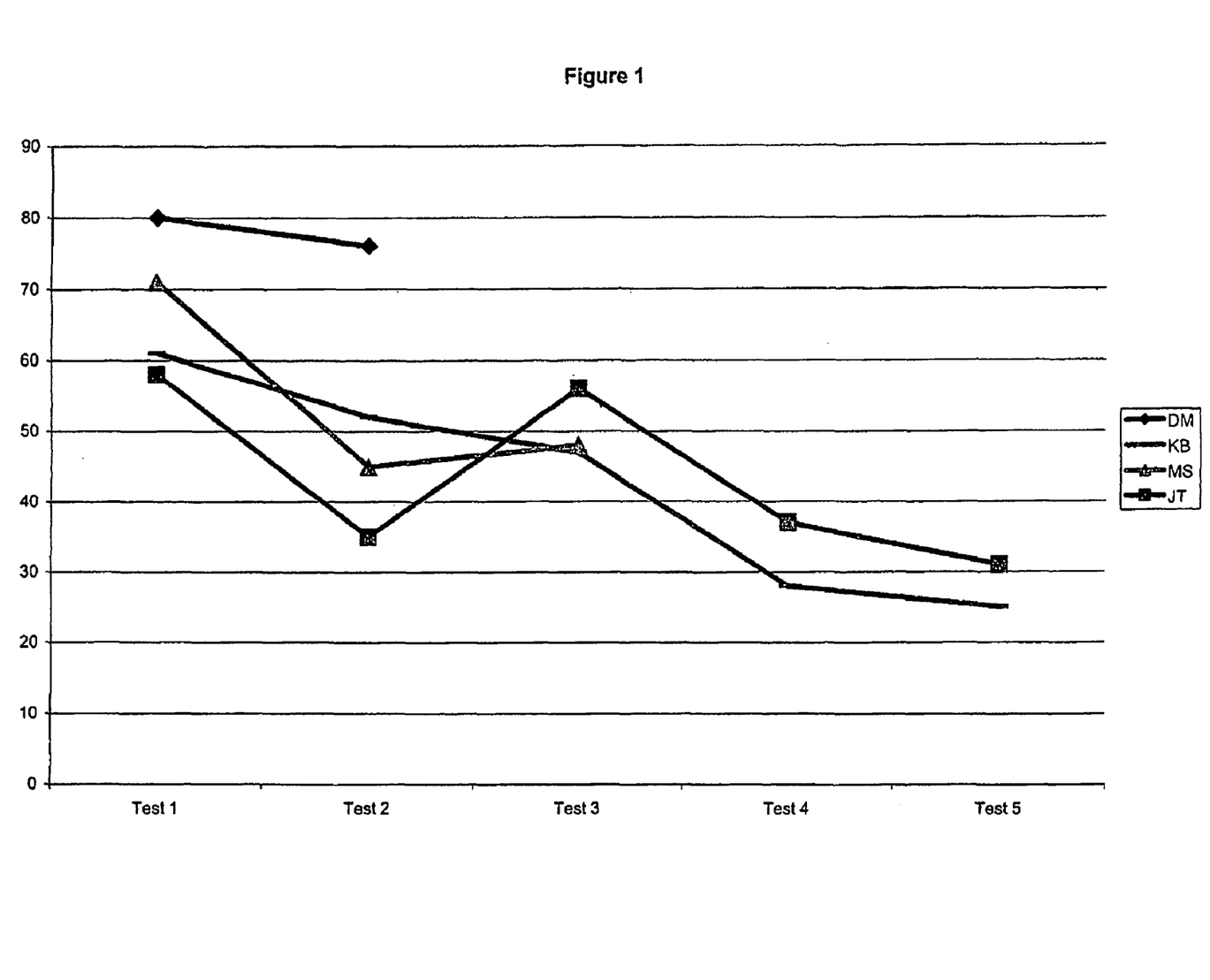
FIG. 1 shows the total MFIS score of the trial patients JT, KB, DM and MS in the Trial Examples of the present invention as described herein, where the MFIS score is along the Y axis and each test is along the X axis.
Figure 4:
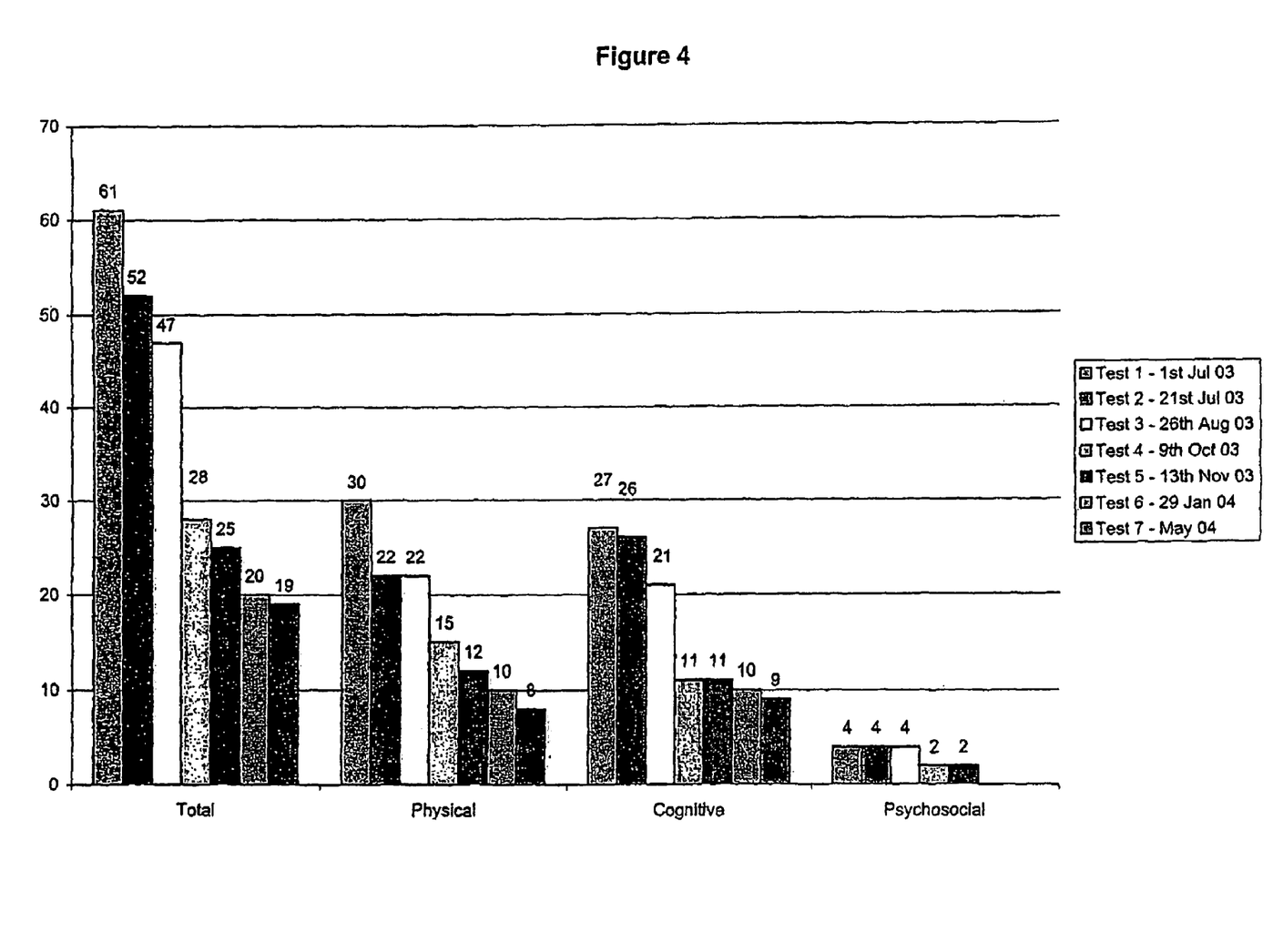
FIG. 4 is similar to FIG. 2 but for patient KB.
Figure 5:
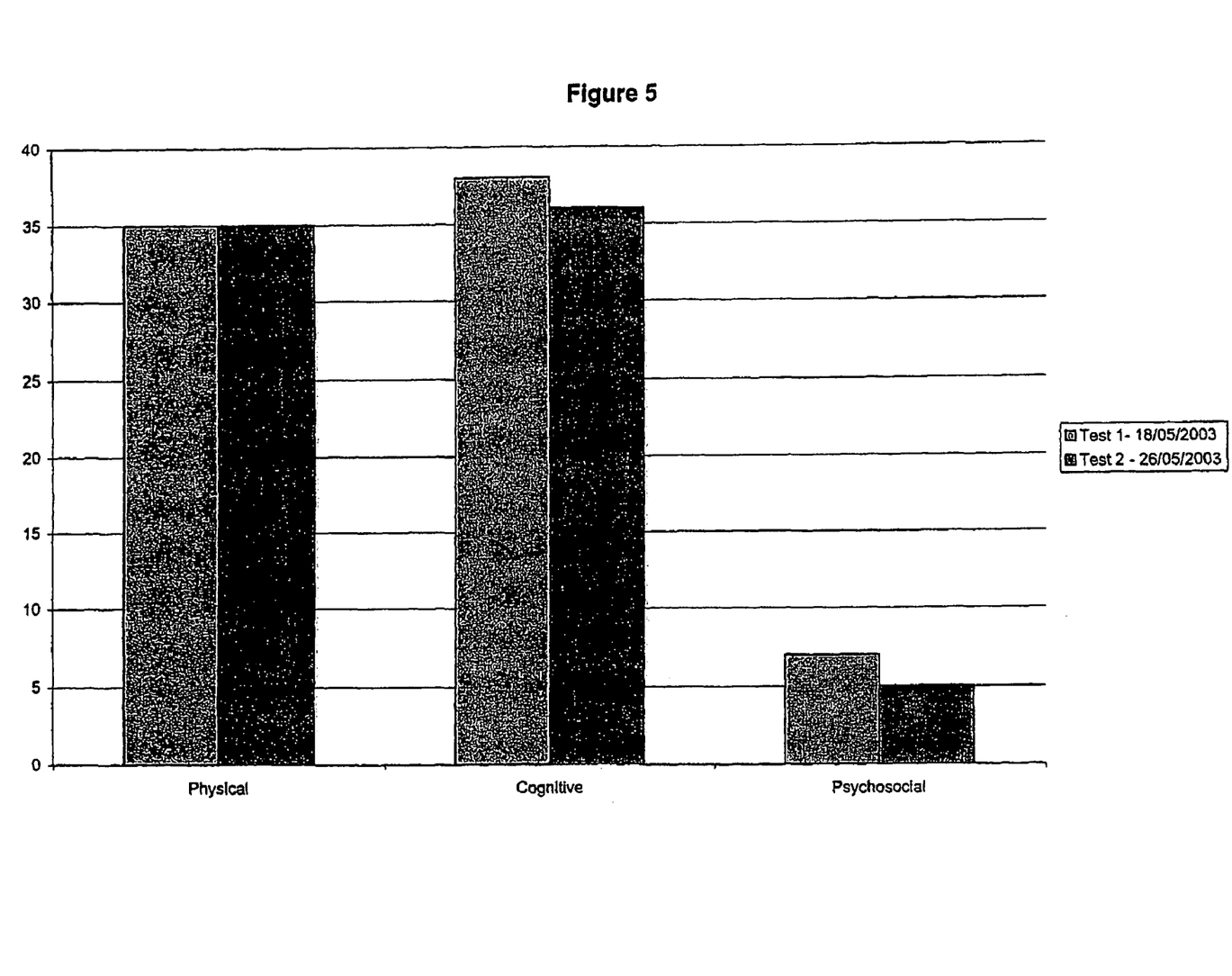
FIG. 5 is similar to FIG. 2 but for patient DM.
Figure 6:
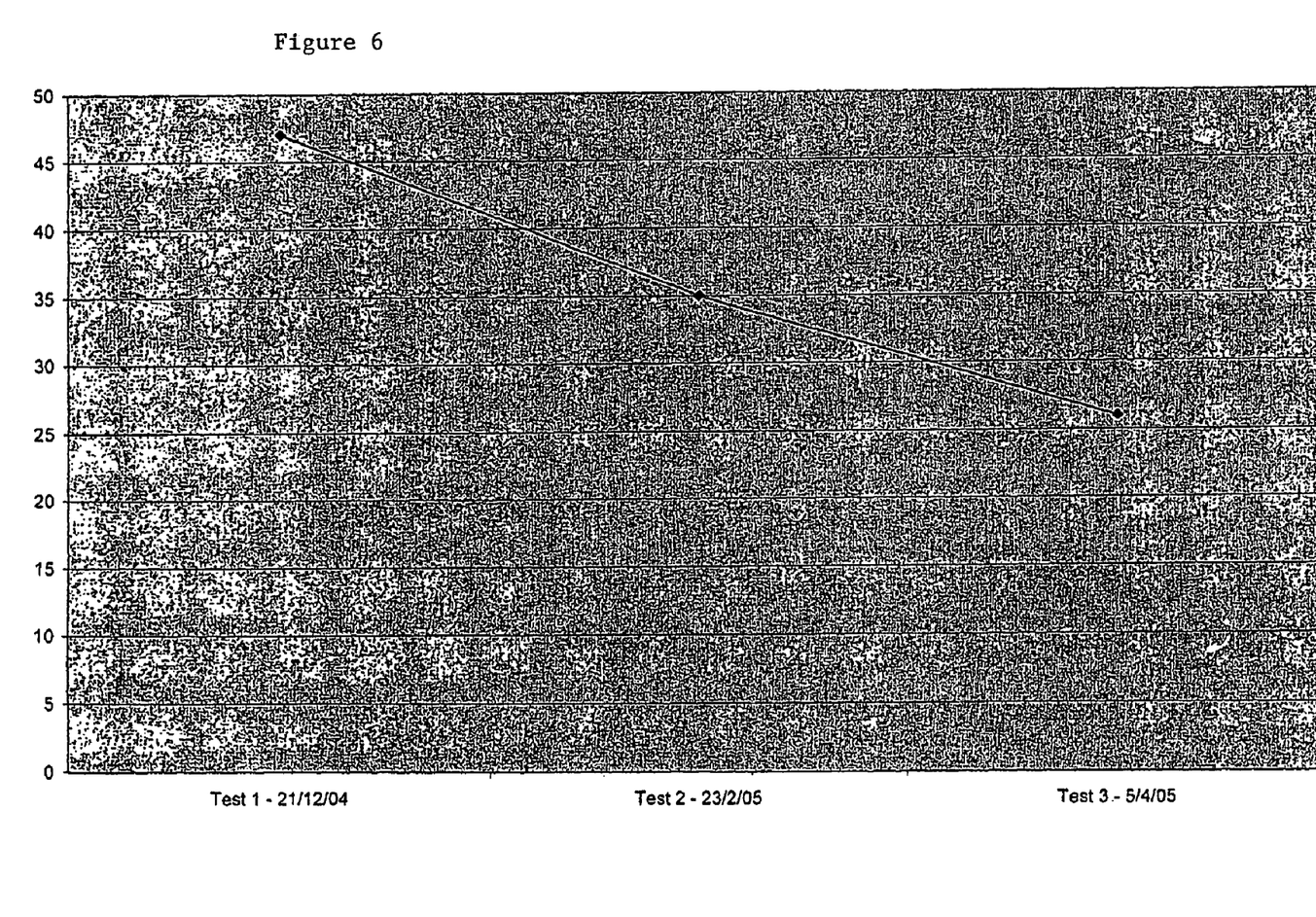
FIG. 6 is similar to FIG. 1 but for patient MB.

KB's initial score indicated a total of 61 on the MFIS scale (see FIGS. 1 and 4).

She was subsequently tested over a period from the first test being conducted from:
First: 1 Jul. 2003
Second: 21 Jul. 2003
Third: 26 Aug. 2003
Fourth: 9 Oct. 2003
Fifth: 13 Nov. 2003

In her latest fatigue score, her total is now 25 verses the previous 61.

KB had also noticed an improvement in the function of her left leg, the area where she had the weakness in the past.

She was very impressed with the use of the capsules and the fact that she had had no reoccurrence of her multiple sclerosis symptoms.

Her MRI scan was completed on the 11.03.05 to ascertain as to any changes over this period.

The comparison shows that there are one or two further lesions but overall there does not seem to be any great progression of the disease since the previous MRI scan.

She continues to use the capsules and feels that they are keeping her multiple sclerosis in check.

Patient GT is Male
D.O.B: 19 Nov. 1958 AGE: 47 years old

GT has a neuritis involving the optic nerve with some loss of vision. GT had his initial MRI scan which was conducted on the 30 Nov. 1998 at which time a diagnosis of multiple sclerosis was made.

GT was seen by Dr EM who told him of the diagnosis and said that he should be using aspirin to reduce his episodes.

He had a consultation with Dr. TM in July 2002, upon where his symptomatology was discussed and he embarked on a course of 4 capsules containing cetyl myristate and cetyl palmitate as described herein ×3 daily because of the extreme fatigue that he suffered.

A daily record was kept regarding GT's multiple sclerosis problem.

His fatigability improved over a period of time and he was able to function again, working 20 hours a week as a carpenter.

GT has continued on using the capsules over this period of time and has had no relapses of his multiple sclerosis problem.

He has regained his strength in his lower limbs which were affected by the multiple sclerosis and feels he is functioning quite normally.

He tends to have some weakness of the muscles of the left eyelid but other than that problem he is functioning very normally.

A subsequent MRI scan was done on 4 Mar. 2005 and compared with his earlier one of the 30 Nov. 1998, said there had been some progression in his cerebral lesions since this time, previous lesion on the right side of the medulla and left side of medulla were unchanged, but there had been some increase in lesions in the cerebral area.

A comment from the MRI scan results that there had been some progression of Multiple Sclerosis changes since the 1998 MRI scan, as we have no records in that ensuing five years, we have had to believe that there may be some arresting of the multiple sclerosis.

GT continues to be very satisfied with the use of the capsules with no side effects and the greatly improved quality of life.

Patient DM is Female
DM is severely disabled from MS.

At her first appointment on 9 Jun. 2002, DM carried out the MFIS questionnaire to determine her total MFIS score which started at 80 (see FIG. 1). DM was then provided with capsules containing cetyl myristate and cetyl palmitate in accordance with the invention described herein which were taken in groupings of 4 capsules 3 times a day.

After 9 days she carried out a second MFIS questionnaire to determine her total MFIS score which had decreased to below 80 (see FIG. 1).

Patient MS is Male

MS was diagnosed with Multiple sclerosis and was prescribed with injections of vitamin B12 injections. In addition he received METFORMIN™ for his diabetes.

At his first appointment on 22 Dec. 2002, MS carried out the MFIS questionnaire to determine his total MFIS score which started at 71 (see FIG. 1). DM was then provided with capsules containing cetyl myristate and cetyl palmitate in accordance with the invention described herein which were taken in groupings of 4 capsules 3 times a day.

After almost one month he carried out a second MFIS questionnaire to determine his total MFIS score which had decreased to 45 (see FIG. 2). MS has subsequently stopped taking the capsules.

Patient MB is Male
D.O.B: 30 May 1946 AGE: 65 years old

MB had been diagnosed with multiple sclerosis approximately 5 years ago and he had noticed a balance problem with tingling in both his legs and fatigue.

He had been seen by Dr EW approximately 5 years ago and had an MRI scan done which confirmed the condition.

Looking at his past history he does relate that the multiple sclerosis may have started from 15 years ago.

His current medication including evening primrose, Omega 3 is Vitamin E, B complex and some Magnesium.

He was seen by Dr TM and started on capsules containing cetyl myristate and cetyl palmitate as described herein on 23 Jan. 2005. The dosage he was given was 4 capsules ×3 daily.

He was then seen by Dr TM in follow-up on 22 Feb. 2005 and stated that he had had some decrease in the tingling in his feet and he was able to actually feel the carpet.

He had continued on with the capsules and completed the Modified Fatigue Impact Scale, hereafter referred to as "MFIS" (Fisk et al. Measuring the functional impact of fatigue: initial validation of the fatigue impact scale. *Clin Infect Dis*. 1994b January; 18 Suppl 1:S79-83). His MFIS score was taken initially at the beginning and subsequently on the 21 Dec. 2004, 23 Feb. 2005 and the 5 Apr. 2005.

His initial total fatigue score was 47 and second test was dropped to 35 and the following test was 26.

MB noted that there was a significant improvement in his overall ability to function.

He is very content with the fact that the capsules have improved the quality of life and in discussing the tingling in his legs he refers to the fact that if you score 1 out of 10, the original feeling was at 3 million, being an excessive exaggeration but at this time it is now down to 3.

Patient JM is Female
D.O.B: 9 Jun. 1974 AGE: 31 years old

JM was initially seen in a consultation with Dr TM on the 15 Jan. 2003. She was a multiple sclerosis patient.

JM had a 10-year history of multiple sclerosis and was initially seen by a physician in 1993 and had an MRI done at that time which confirmed the presence of lesions in the cerebella which confirmed the diagnosis for multiple sclerosis.

JM was seen Dr EM and placed on Interferon to try and reduce her recurrence episodes of the multiple sclerosis attacks.

She was seen in consultation by Dr TM in January 2003 and began taking capsules containing cetyl myristate and cetyl palmitate as described herein.

Since then she has been well with only 2 episodes of recurrence. One of these episodes was in approximately January 2004 when prior to her new marriage, anxiety and tension had precipitated a slight weakness that she attributed to a multiple sclerosis episode. This resolved after approximately 4 weeks. She remained well up until March of this year when she had an episode of vertigo and nausea. She was admitted to hospital and was thought to have suffered labyrinthitis, possibly benign positional labyrinthitis or viral.

This was not directly attributed to the multiple sclerosis although a question must be raised if there had been any quick recurrence.

She is confident in the use of the capsules according to the present invention and continues to rely on these because her fatigue had improved during the course of her use of the capsules. She has completed the Modified Fatigue Impact Scale, hereafter referred to as "MFIS (Fisk et al. Measuring the functional impact of fatigue: initial validation of the fatigue impact scale. Clin Infect Dis. 1994b January; 18 Suppl 1:S79-83). Her initial fatigability score was 58 of 70 possible and in November 2004 it was 24, which allowed her to function in a more normal manner.

Summary of Results

The compliance has been excellent with patients accepting the capsules containing cetyl myristate and cetyl palmitate according to the present invention and they have used the capsules with no side effects. The benefit to the multiple sclerosis patients is that there is a decrease in fatigability and a marked decrease in recurrence. Also there is an indication that there is some return of function to the previously affected areas.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, the terms "comprising", "including", "containing", etc. are to be read expansively and without limitation.

The invention claimed is:

1. A method of ameliorating multiple sclerosis-induced fatigue and/or tingling in a mammal afflicted with multiple sclerosis, which comprises
   administering or having self administered to such mammal an amount effective for ameliorating multiple sclerosis-induced fatigue and/or tingling of a medicament consisting of cetyl myristate and one or both of an excipient and a diluent, or a medicament consisting of cetyl myristate, cetyl palmitate and one or both of an excipient and a diluent.

2. The method according to claim 1 wherein the administration is oral.

3. The method according to claim 1 wherein the administration is of a medicament consisting of a mixture of cetyl myristate, cetyl palmitate and one or both of an excipient and a diluent.

4. The method according to claim 2, wherein the cetyl myristate comprises at least 50% w/w of the mixture.

5. The method according to claim 2, wherein the ratio of cetyl myristate to cetyl palmitate w/w in the medicament is in the range of 80:20 to 99:1.

6. The method according to claim 4, wherein the ratio of cetyl myristate to cetyl palmitate w/w in the medicament is 95:5.

7. The method according to claim 1 wherein the administration is of one or more capsules.

8. The method according to claim 1 wherein the administration is of a liquid.

9. The method according to claim 1 wherein the mammal is a human being.

10. The method according to claim 1 wherein the fatigue is ameliorated.

* * * * *

UNITED STATES PATENT AND TRADEMARK OFFICE
CERTIFICATE OF CORRECTION

PATENT NO. : 8,299,120 B2
APPLICATION NO. : 11/628266
DATED : October 30, 2012
INVENTOR(S) : Dianne Cadwallader et al.

It is certified that error appears in the above-identified patent and that said Letters Patent is hereby corrected as shown below:

On Title page, in field (73), in "Assignee", in column 1, line 1, delete "Lypanosis Pte Limited," and insert -- Lypanosys Pte Limited --

Signed and Sealed this
Nineteenth Day of February, 2013

Teresa Stanek Rea
*Acting Director of the United States Patent and Trademark Office*